(12) United States Patent
Hilpert et al.

(10) Patent No.: US 6,823,721 B1
(45) Date of Patent: Nov. 30, 2004

(54) METHOD AND SYSTEM FOR MASS FLOW BALANCE ACCOUNTING

(75) Inventors: Lee Hilpert, Livingston, TX (US); Gary L. Hensley, Kingwood, TX (US)

(73) Assignee: Hutchison Hayes, L.P., Houston, TX (US)

( * ) Notice: Subject to any disclaimer, the term of this patent is extended or adjusted under 35 U.S.C. 154(b) by 0 days.

(21) Appl. No.: 10/316,804

(22) Filed: Dec. 11, 2002

Related U.S. Application Data

(60) Provisional application No. 60/341,196, filed on Dec. 13, 2001.

(51) Int. Cl.[7] .......................... G01N 33/24; B01D 45/12
(52) U.S. Cl. .................... 73/61.41; 73/61.59; 73/61.61; 73/61.71; 73/61.72; 73/152.18; 73/152.23; 73/152.42; 175/40; 175/66; 175/206; 175/207; 210/85; 210/322; 210/767; 210/787
(58) Field of Search .......................... 73/61.41, 61.59, 73/61.61, 61.71, 61.72, 152.04, 152.18, 152.23, 152.42; 175/40, 50, 66, 206, 207; 210/85, 322, 767, 787

(56) References Cited

U.S. PATENT DOCUMENTS

| | | | | |
|---|---|---|---|---|
| 4,624,327 A | * | 11/1986 | Reichman | 175/67 |
| 4,635,735 A | * | 1/1987 | Crownover | 175/48 |
| 5,010,966 A | * | 4/1991 | Stokley et al. | 175/66 |
| 5,993,049 A | | 11/1999 | Sheldon | |
| 6,036,862 A | * | 3/2000 | Stover | 210/603 |
| 6,443,001 B1 | * | 9/2002 | Duriez et al. | 73/152.19 |

* cited by examiner

*Primary Examiner*—Daniel S. Larkin
(74) *Attorney, Agent, or Firm*—Law Office of Tim Cook P.C.

(57) ABSTRACT

A system which receives as inputs various measurements of solids and liquids in a clarification system and, from these measurements, determines the various constituents and their fractional makeup within the system. The measurements may be made manually or mechanically, but are preferably made manually. From a quantitative analysis of easily accessible sample points, data is acquired and plugged into a spread sheet program, which numerically and graphically displays the breakdown of the constituents which make up the solids and liquids discharged from a treatment stage or of the entire system.

6 Claims, 3 Drawing Sheets

METHOD AND SYSTEM FOR MASS FLOW BALANCE ACCOUNTING

This application claims the benefit of U.S. Provisional Application Ser. No. 60/341,196 filed Dec. 13, 2001.

BACKGROUND OF THE INVENTION (1) Field of the Invention

The present invention relates generally to fluid clarification systems and, more particularly, to a system and method of determining the fraction of the various constituents resulting from the clarification system as a whole, or from one or more stages within the clarification system. The present invention is broadly applicable to systems in which solids are separated from liquids, or systems in which one liquid is separated from another liquid, or systems in which an incoming feed is split into at least two portions. However, the present invention is particularly adapted to systems for removing cuttings from drilling fluid in which the fractions of oil, water, and solids are to be determined.

(2) Description of Related Art

The present invention provides a system and method of accounting for solids and liquids at various points in a drilling mud treatment system used with a drilling rig. When an oil well is drilled, it is necessary to drill the well with drilling fluid, commonly referred to in the art as drilling mud. The drilling mud is provided to lubricate and cool the drill bit and to carry away cuttings as the mud flows upwardly in the annular flow space around the drill string. The drilling mud is pumped down the drill string to pick up the cuttings and other debris. Commonly, the drilling mud is either a water-based or an oil-based carrier.

When drilling into a high pressure formation or at great depths, safety is enhanced by incorporating a weight component, such as barium sulfate, barite, or hematite, for example, to the drilling mud to increase the weight of the drilling mud. The additives are expensive and various systems have been proposed for the recovery and recycling of drilling mud additives. Also, when drilling mud circulates through the well it picks up particles or cuttings of the earth formations cut by the drill bit. Various systems have therefore been proposed to remove the cuttings from the drilling mud so that the drilling mud can be recycled for further use in drilling operations.

Even very effective systems for removing cuttings from the drilling mud leave some mud adhering to the cuttings. For offshore drilling operations, this is particularly serious because drilling mud contains substances which are harmful to the environment, and when the cuttings are jettisoned over the side of the drilling platform, they carry deleterious substances with them into the water. Regulations in various jurisdictions around the world place strict limits on the overall quantity of such drilling mud constituents which can be discharged into the sea, and thus it is vitally important to account for all constituents of the drilling mud. It is also vital to keep track of the drilling mud, because it is a valuable commodity and every barrel of drilling mud recycled for reuse represents substantial savings to the user. Further, it is also vital to account for all the drilling mud because of the limits placed on its discharge.

Thus, there remains a need for a system which can quickly, easily, and graphically display the fractional or absolute quantities of the constituents of drilling mud. The present invention is directed to such a system.

SUMMARY OF THE INVENTION

The present invention addresses these and other needs in the art by providing a system which takes as inputs various measurements of solids and liquids in a clarification system and, from these measurements determines the various constituents and their fractional makeup within the system. The measurements may be made manually or mechanically, but in the preferred embodiment the measurements are made manually. From a quantitative analysis of easily accessible sample points, data is acquired and plugged into a spread sheet program, which numerically and graphically displays the breakdown of the constituents which make up the solids and liquids discharged from a treatment stage or of the entire system.

Thus, the present invention provides a method that resolves volumetric fractional contributions of a solids discard stream of a centrifuge or a dryer when the feed rate, volumetric fractions of the various constituents of the feed stream, and the volumetric fractional contributions of one of the constituents of the liquid discharge stream are known. The method of the invention does this based on the recognition that given a feed rate, with its given volumetric fractions, and further given one of the volumetric fractions of any constituents in the subsequent streams made up of the feed stream, there is only one solution which allows the total volumetric balance of the feed streams as compared to the subsequent streams.

Thus, in one aspect, the present invention provides a mass balance accounting system in a clarification system having at least one clarification stage. The accounting system comprises three basic elements: a means for measuring the flow rate into the clarification system; a means for measuring the constituents resulting from the clarification stage(i.e. oil, water, and solids); and an interdependent calculator to receive the measured constituents and determine the fractional contributions of the constituents from the clarification stage.

In a further aspect of the invention, a method of determining and displaying the effectiveness of the clarification system or a clarification stage is provided.

These and other features and advantages of the present invention will be apparent to those skilled in the art from a review of the following detailed description along with the accompany drawings.

BRIEF DESCRIPTION OF THE DRAWINGS

The appended drawings illustrate only typical embodiments of this invention and are therefore not to be considered limiting of its scope, for the invention may admit to other equally effective embodiments.

DETAILED DESCRIPTION OF PREFERRED EMBODIMENTS

Figure 1:
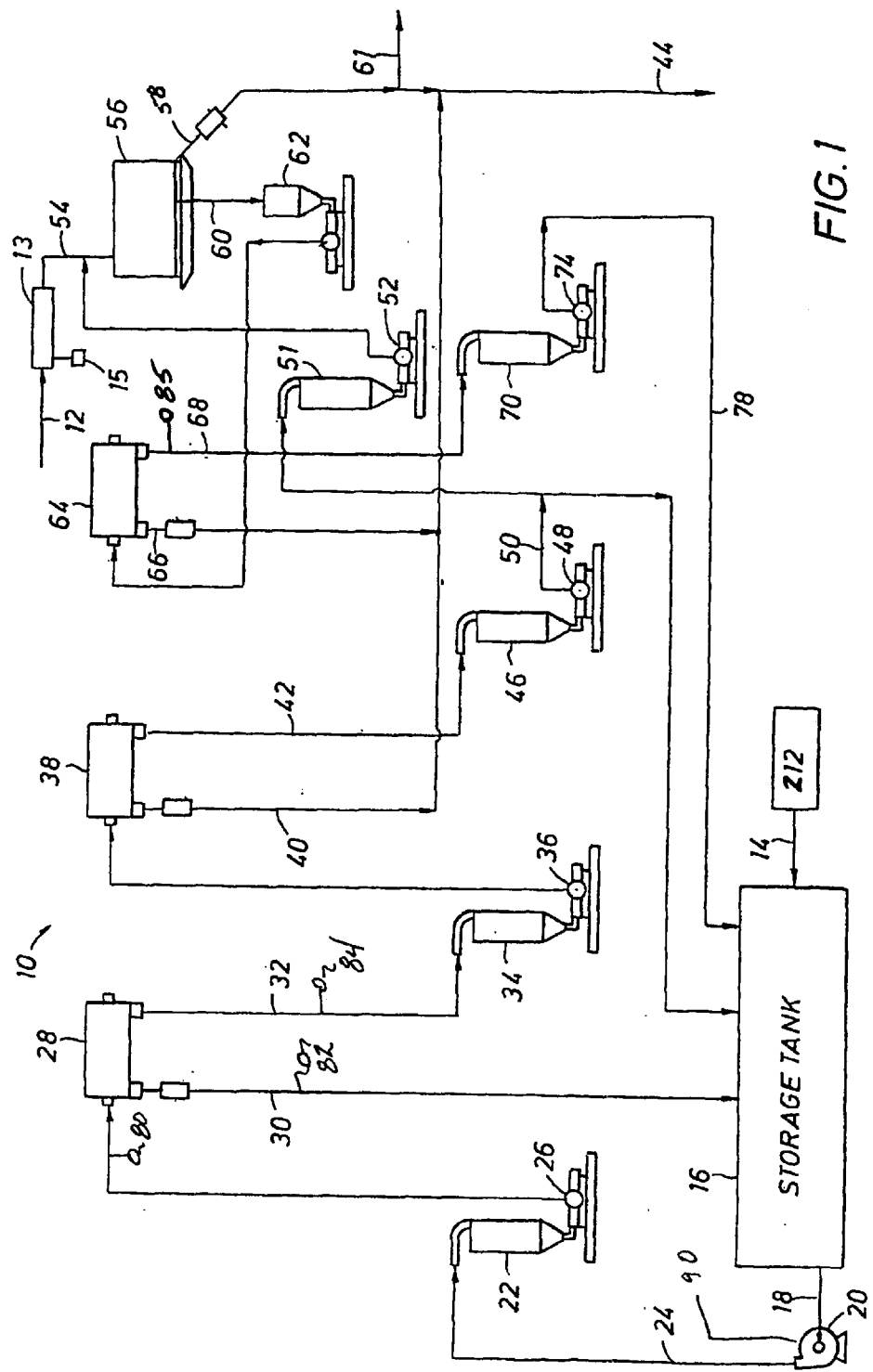
FIG. 1 is an overall schematic diagram of a drilling mud treatment system in which the present invention finds application.

FIG. 1 depicts a mud clarification or processing system 10, wherein the present invention may be applied. It is to be understood by those skilled in the art that the teachings of the invention are applicable to other separation systems, as well. Initially, drilling mud returned from downhole is delivered to mud pits and thence is transferred to a shale shaker 212. The supply line from the shale shaker is shown schematically in FIG. 1 with the reference number 12 into a transporter 13 having a discharge line 54. Element 15 depicts a sensor which determines the mass flow rate of feed through the transporter 13. The shale shaker picks up large particles which are collected on a screen in the shale shaker for removal from the mud. From the shale shaker, a mud line 14 is connected into the system 10, thereby supplying recirculated drilling mud into the system.

Supply of drilling mud enters the system from the mud line 14 into a storage tank 16, although it should be understood that a plurality of such storage tanks are preferably used. Drilling mud from the storage tank 16 is directed through a supply line 18 into a first positive displacement pump 20.

Mud is pumped by the pump 20 into the inlet of a first mass flow sensor 22 by way of a supply line 24. The mud is then pumped from the mass flow sensor 22 by a pump 26 into a first stage centrifuge 28. The first stage centrifuge is controlled to separate the desirable, heavy components which have been added to the drilling mud, while passing the lighter weight cuttings along with drilling mud.

As viewed in FIG. 1, a solids discharge 30 from the centrifuge 28 is on the left, and a liquids discharge 32 is on the right. The solids discharge 30, including the high value, high gravity solids, is returned to the tank 16, thereby restoring the high gravity solids to the system for further use. The liquids discharge 32, carrying water or oil-based drilling fluid along with low gravity solids (cuttings) is directed to a second mass flow sensor 34. The mud is then pumped by a pump 36 into a second stage centrifuge 38 which is controlled in its speed and torque to remove low gravity solids, i.e. cuttings, from the mud. As before with regard to the first stage centrifuge 28, a solids discharge 40 from the second centrifuge is depicted on the left in FIG. 1 and a liquids discharge 42 is depicted on the right. The solids discharge 40 is directed to a disposal line 44 for discharge. It should be understood that, although the solids discharge disposal line 44 is shown as a single line, the system may include a number of such discharge lines over the side or into a capture system. The liquid discharge 42 is directed to a third mass flow sensor 46.

From the third mass flow sensor 46, the now substantially clarified drilling mud is pumped by a pump 48 into a line 50 where the mud may be directed to the tank 16 and/or to a fourth mass flow sensor 51 and then to the suction of a booster pump 52. The booster pump 52 directs the flow to a cuttings inlet line 54 where cuttings from the shale shakers are received. The cuttings inlet line 54 flows into a cuttings dryer 56. The solids from the cuttings dryer 56 are directed to a solids discharge line 58 and to the disposal line 44 for discharge, and the liquids from the cuttings dryer 56 are directed to a liquid discharge line 60 and to a fifth mass flow sensor 62. Alternatively, the cuttings dryer 56 may be provided with a discharge line 61, separate from the disposal line 44, to direct its solids discharge for disposal. From the mass flow sensor 62, the mud is pumped to a third stage centrifuge 64. The solids from the third stage centrifuge 64 are directed to a solids discharge line 66 and to the disposal line 44. The liquids from the third stage centrifuge 64 are directed to a liquids discharge line 68 into a sixth mass flow sensor 70. The mud is then pumped by a pump 74 over a line 78 back to the tank 16 for further use.

It should now be appreciated that determining effectiveness of the system in removing solids from a feed stream at the various stages is a complex and difficult task, absent the present invention. It would be very useful to know the breakdown of the constituents at various points in the system, or for the system as a whole, in order to determine the effectiveness of the clarification system. Determining the fractional makeup of the various constituents also determines cost savings in recycling the expensive constituents of the feed and verifies that regulations for the discharge of constituents are met. In order to provide that data necessary for input to the mass balance accounting system of the present invention, various sample points are provided in the system, such as for example a feed rate sensor 90 at the pump 20 to provide the volumetric flow of feed to the system 10. A sample point 80 is also provided to capture a specimen of the feed into the separator 28. Samples taken from the sample point 80 are preferably titrated to determine the volume percent or absolute flow rate of high and low gravity solids, water, and oil at that point. Similarly, sample point 82, 84, and 85 are provided to capture specimens at those points. In carrying out the invention, samples are taken at the sample points 82, 84, and 85, along with data from sensors within the system 10, and the samples are titrated to determine the makeup of the drilling mud at those locations. The titration results are then input into a computer, which performs calculations in accordance with teaching of this disclosure, as described below.

Figure 2:
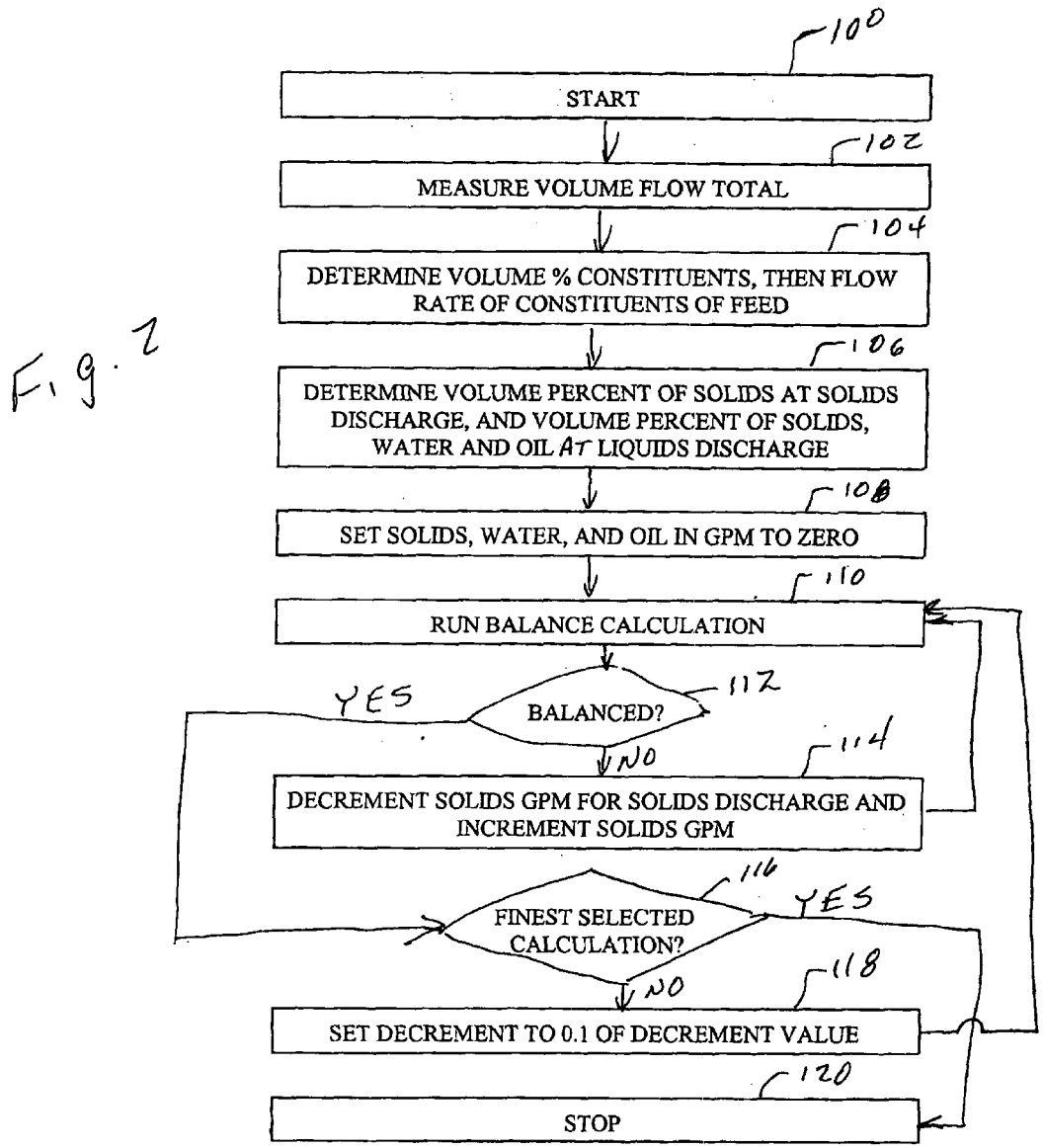
FIG. 2 is a logic flow diagram of a preferred embodiment of the mass flow accounting system of the invention.

FIG. 2 depicts a preferred embodiment of the logic flow of the invention. The logic begins with step 100 in which the system is initialized. Step 102 involves measuring the volumetric flow rate of feed into the system, such as for example by determining the feed rate of the pump 20 by means of the flow sensor 90. From a titration, or other means of measurement, of a specimen taken at the sample point 80, the volume percent of solids, water, and oil are then determined in step 104. Knowing the total feed rate in gpm, the volumetric flow rate of these constituents is then calculated, also in step 104. The calculation performed in step 104 thus provides a base data point for the constituents in the drilling mud prior to treatment by the treatment system 10.

In step 106, a determination is made in respect of the constituents after some treatment of the stream, such as for example, immediately after the first separator 28, by specimens taken from sample points 82 and 84. Alternatively, the specimens could comprise the samples taken from liquid return lines to the storage take 16 and the solids discharge line 44. Step 106 thus involves a determination of the volume percent of the solids in the solids discharge, and volume percents of the solids, water, and oil in the liquids discharge. These data form the basis of the determination of the effectiveness of the clarification step, or the system.

Figure 3:
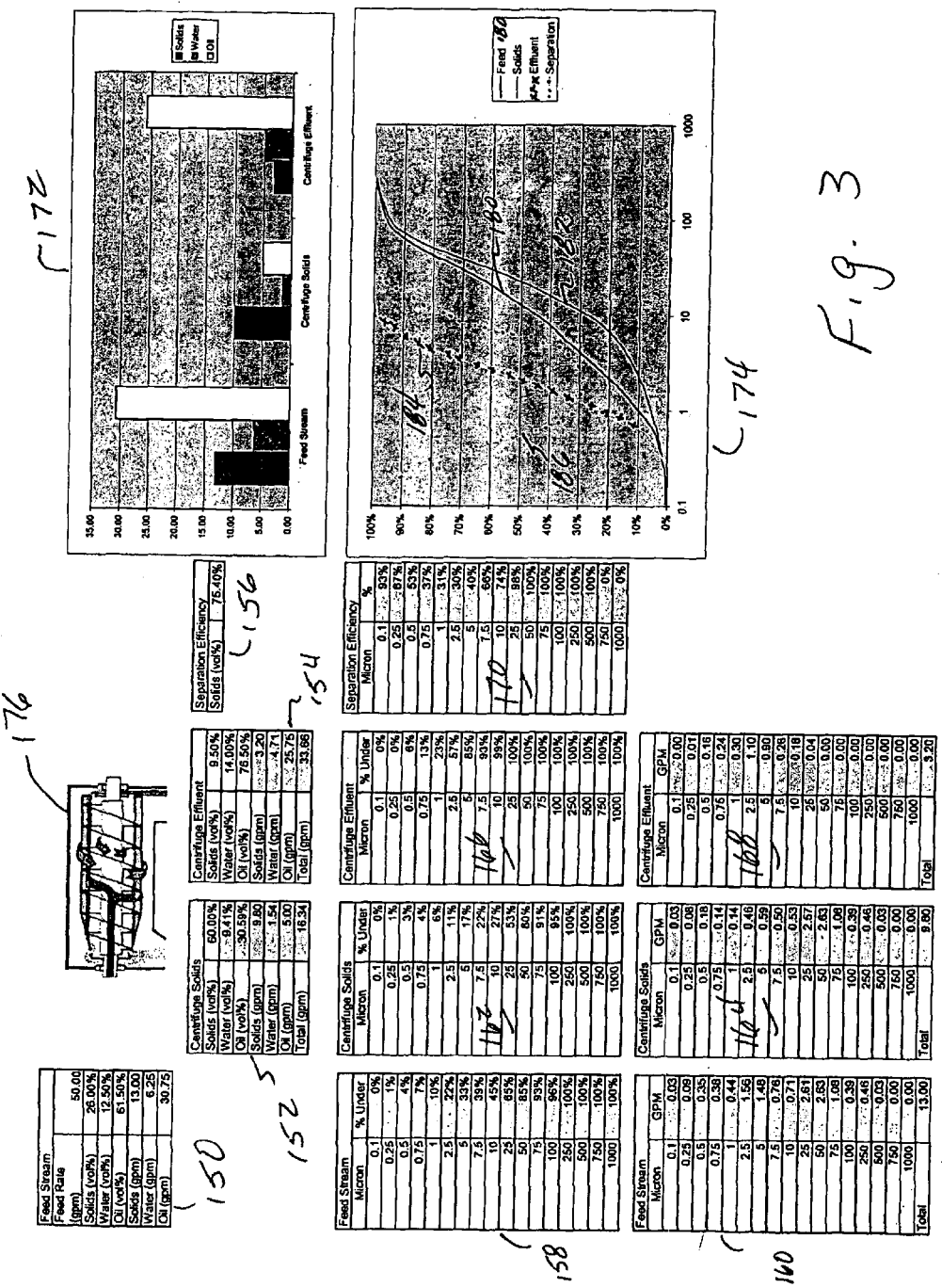
FIG. 3 is a display of a graphical user interface of the invention.

Attention is now directed to FIGS. 2 and 3 simultaneously. FIG. 3 depicts a graphical user interface of the working of the invention. Element 176 of FIG. 3 illustrates a centrifugal separator, having a solids discharge with data shown in a table, labeled as element 152, and a liquids discharge with data shown in a table, labeled as element 154. The data determined in step 106 are shown now entered into the tables 152, 154, and 156.

Step 108 comprises setting the values in table 154 for solids, water, and oil to zero. The various tables shown in FIG. 3 are preferably determined by a spreadsheet program, in which the entries are interdependent, and the alteration of one datum alters the values of other entries. With the values of volumetric flow of solids, water, and oil in table 154 set to zero, these values in table 152 will be the same as the volumetric flow of the feed stream table, labeled 150. But, these values are known to be wrong, from the analyses of the discharges on the solids and liquids sides of the separator 176, and this result is concluded by step 110 when comparing the known solids volume percent and the known constituents values of the liquids side. So, step 112 at this point determines that the numbers in the tables 152 and 154 do not balance. In step 114, the solids gpm is decremented from its initial value, (13 gpm from table 150) and the solids gpm in table 154 is incremented. Also initially, the decrement and increment values are set at one, and the user is provided with the option of how many digits (i.e. how fine) to determine the fractional percentages of the various constituents.

Once the volumetric flow entries from solids in tables 152 and 154 have been decremented and incremented, respectively, the balance calculation is again run in step 110, and step 112 checks to see if the constituents balance. Steps 110 through 114 are repeated until balance is attained, then number of times the steps are repeated depending on how fine the determination of fractional percentages set by the user. Once the values of the constituents balance, then a determination is made in step 116 as to whether the selected number of digits have been run, for the fineness of the balance determination. If the fineness has not yet been reached, then the increment/decrement number is set to 0.1 of the previous value in step 118, and the logic returns to step 110 to again run the balance calculation. Once the selected number of digits has been determined in the balance control calculation, the logic stops in step 120.

FIG. 3 also provides a graphical depiction of the results of these calculations. In element 172, the volumetric flow of solids, water, and oil in the feed stream, the solids discharge, and liquids discharge are depicted. This provides a vivid image to the user of the effectiveness of that particular separation stage. The plot of element 174 depicts the various values of feed rate 180, solids 182, and liquids effluent 184, and the effective separation 186 for various flow rates through the system. These values are also depicted in tabular form in elements 158 through 170, inclusive.

The principles, preferred embodiment, and mode of operation of the present invention have been described in the foregoing specification. This invention is not to be construed as limited to the particular forms disclosed, since these are regarded as illustrative rather than restrictive. Moreover, variations and changes maybe made by those skilled in the art without departing from the spirit of the invention.

We claim:

1. A mass balance accounting system in a clarification system having at least one clarification stage, the accounting system comprising:

(a) means for measuring the flow rate of a mixture of constituents into the clarification system, the constituents comprising oil, water, and solids;

(b) means for measuring the constituents resulting from the clarification stage; and (c) an interdependent calculator to receive the measurements of the constituents from step 1(*b*) and determine the fractional contributions of the constituents from the clarification stage.

2. The system of claim 1, wherein the means for measuring the constituents includes a first stage sample point before the clarification stage and a second stage sample point after the clarification stage.

3. The system of claim 1, further comprising a plurality of clarification stages, and wherein the means for measuring the constituents includes a first system sample point before the plurality of clarification stages and a second system sample point after the plurality of clarification stages.

4. The system of claim 1, further comprising a graphical display showing the fractional contributions of the constituents from the clarification stage.

5. A method of measuring the performance of a clarification system adapted to separate oil, water, and solids constituents of a mixture, comprising the steps of:

a. measuring the flow rate of the mixture into the clarification system;

b. measuring the fractional contribution of each of the oil, water, and solids constituent into the clarification system;

c. determining the fraction of constituents separated by the clarification system; and d. running a mass flow balance equation to determine the flow rate of the constituents resulting from the clarification system, thereby determining the performance of the clarification system by determining quantitatively the fraction of each constituent.

6. The method of claim 5, further comprising the step of displaying the result of the mass flow balance equation on a graphical user interface.

\* \* \* \* \*